US008406448B2

(12) United States Patent
Lin et al.

(10) Patent No.: US 8,406,448 B2
(45) Date of Patent: Mar. 26, 2013

(54) EARPHONE WITH ROTATABLE EARPHONE CAP

(75) Inventors: You-ruei Lin, Tu Cheng (TW); Chun-hung Chen, Tu Cheng (TW); Mu-tsun Tseng, Tu Cheng (TW)

(73) Assignee: Cheng Uei Precision Industry Co., Ltd., Tu Cheng, Taipei (TW)

(*) Notice: Subject to any disclaimer, the term of this patent is extended or adjusted under 35 U.S.C. 154(b) by 269 days.

(21) Appl. No.: 12/907,984

(22) Filed: Oct. 19, 2010

(65) Prior Publication Data

US 2012/0093331 A1 Apr. 19, 2012

(51) Int. Cl.

| | |
|---|---|
| ***H04R 25/00*** | (2006.01) |
| ***H04R 1/02*** | (2006.01) |
| ***H03B 29/00*** | (2006.01) |
| ***G10K 11/16*** | (2006.01) |
| ***A61F 11/06*** | (2006.01) |

(52) U.S. Cl. ....... 381/380; 381/71.6; 381/332; 381/370; 381/371; 381/382

(58) Field of Classification Search .................. 381/370, 381/371, 373, 380, 386, 1–124, 300–311, 381/332–336, 382

See application file for complete search history.

(56) References Cited

U.S. PATENT DOCUMENTS

| | | | | |
|---|---|---|---|---|
| 7,697,710 | B2 * | 4/2010 | Yang | 381/382 |
| 8,041,067 | B2 * | 10/2011 | Yang | 381/371 |
| 8,270,648 | B2 * | 9/2012 | Murozaki | 381/328 |
| 2006/0256992 | A1 * | 11/2006 | Liao | 381/371 |
| 2007/0036381 | A1 * | 2/2007 | Klemenz et al. | 381/330 |
| 2009/0103760 | A1 * | 4/2009 | Stiehl et al. | 381/371 |
| 2012/0275635 | A1 * | 11/2012 | Chen | 381/380 |

* cited by examiner

*Primary Examiner* — Nhan T Tran
*Assistant Examiner* — Xi Wang
(74) *Attorney, Agent, or Firm* — Cheng-Ju Chiang

(57) ABSTRACT

Provided is an earphone, including an earphone body and an earphone cap. The earphone body includes an earphone shell forming a sound cavity and disposing a sound-guiding pipe. The sound-guiding pipe disposes at least one through hole. The earphone cap is rotatably mounted on the earphone body and includes a main body and a barrel. The barrel is located on the inside of the main body and arranged to encompass the sound-guiding pipe. The barrel disposes at least one opening, which is arranged to be aligned or misaligned with the part or whole of the through hole. The earphone of the present invention can make the opening be aligned or misaligned with and the part or whole of the through hole by rotating the earphone cap, thereby varying the pressure of the sound cavity to attain the object of adjusting sound effect.

4 Claims, 2 Drawing Sheets

EARPHONE WITH ROTATABLE EARPHONE CAP

BACKGROUND OF THE INVENTION

1. Field of the Invention

The present invention relates to an earphone, and more particularly to an earphone capable of adjusting the sound effect.

2. Description of the Prior Art

With the development of science and technology, electronic products are continuous upgraded. In order to assure that users can listen to the sound generated by the electronic product under the state of not interfering with others, an earphone is served as a necessary accessory of the electronic product.

To the traditional earphone, when needing to adjust the sound in bass range, the pressure inner a rear chamber of the earphone can be varied by placing or not placing a damping object into the rear chamber for changing the damping effect of the earphone. So the sound and the sound pressure in the bass range can be controlled and matched with the sound in the treble range. The damping object also can prevent foreign matters, which may cause noise or destroy the earphone, from entering into the earphone body. But an ordinary consumer cannot freely replace the damping object in the traditional earphone, but receive the sound, which is generated by the earphone and cannot be adjusted. Therefore, the traditional earphone is not convenient in use.

BRIEF SUMMARY OF THE INVENTION

An object of the present invention is to provide an earphone, being capable of adjusting the sound effect in bass range.

To achieve the above object, in accordance with the present invention, an earphone is provided, comprising an earphone body and an earphone cap. The earphone body includes an earphone shell, which forms a sound cavity in inside thereof and disposes a sound-guiding pipe on one end thereof. The sound-guiding pipe disposes at least one through hole. The earphone cap is rotatably mounted on the earphone body and includes a main body and a barrel. The barrel is located on the inside of the main body and arranged to encompass the sound-guiding pipe. The barrel disposes at least one opening, which is arranged to be aligned or misaligned with the part or whole of the through hole.

Based on the above description, the earphone of the present invention can make the opening of the earphone cap be aligned or misaligned with and the part or whole of the through hole of the sound-guiding pipe by rotating the earphone cap, thereby varying the pressure of the sound cavity to attain the object of adjusting sound effect.

DETAILED DESCRIPTION OF THE PREFERRED EMBODIMENTS

The following embodiment with reference to the accompanying drawings now has been given for detail describing the technology, the feature, the object and the effect of the present invention.

Figure 1:
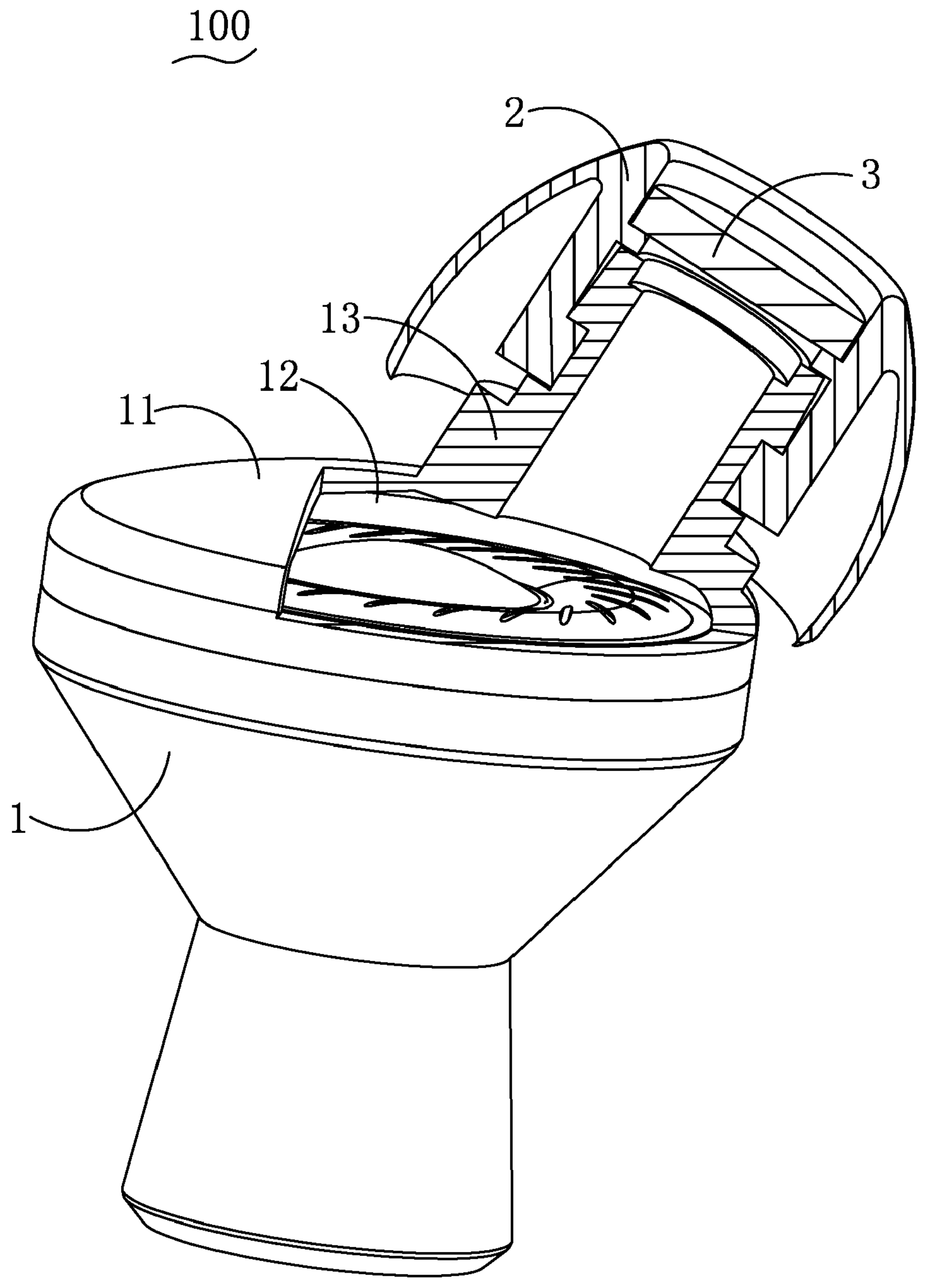
FIG. 1 is a perspective view of an earphone according to one embodiment of the present invention, part of which is showing in section.

Referring to FIG. 1, an earphone 100 of the present invention comprises an earphone body 1, an earphone cap 2 and a reticular spacer 3.

Figure 2:
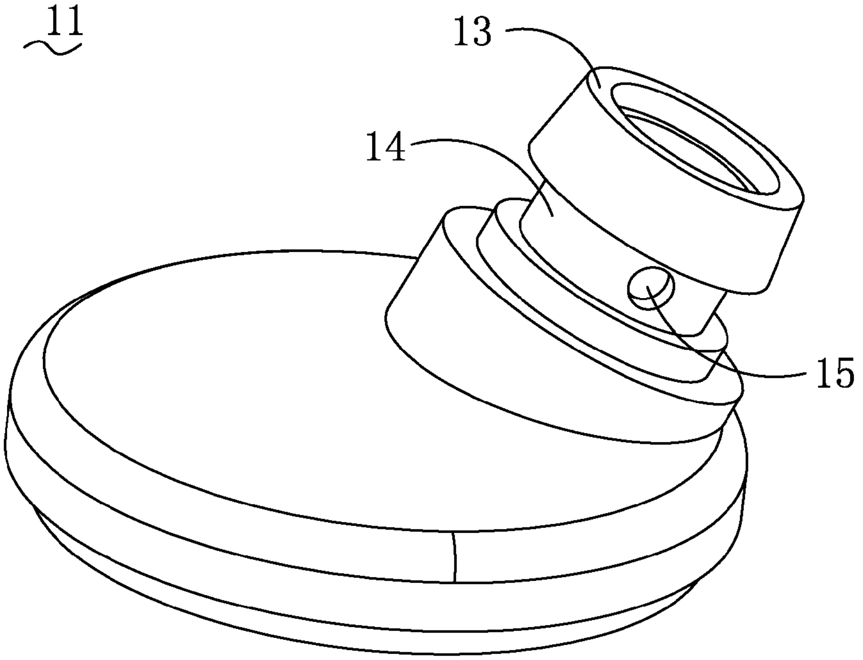
FIG. 2 is a perspective view of an earphone shell of the earphone of FIG. 1.

Referring to FIGS. 1 and 2, the earphone body 1 includes an earphone shell 11, which forms a sound cavity 12 in inside thereof and disposes a sound-guiding pipe 13 on one end thereof. The sound-guiding pipe 13 disposes a through hole 15 passing through an inner surface and an outer surface thereof and an annular groove 14 concavely forming on the outer surface thereof. On one embodiment, the through hole 15 is formed on the location of the annular groove 14.

Figure 3:
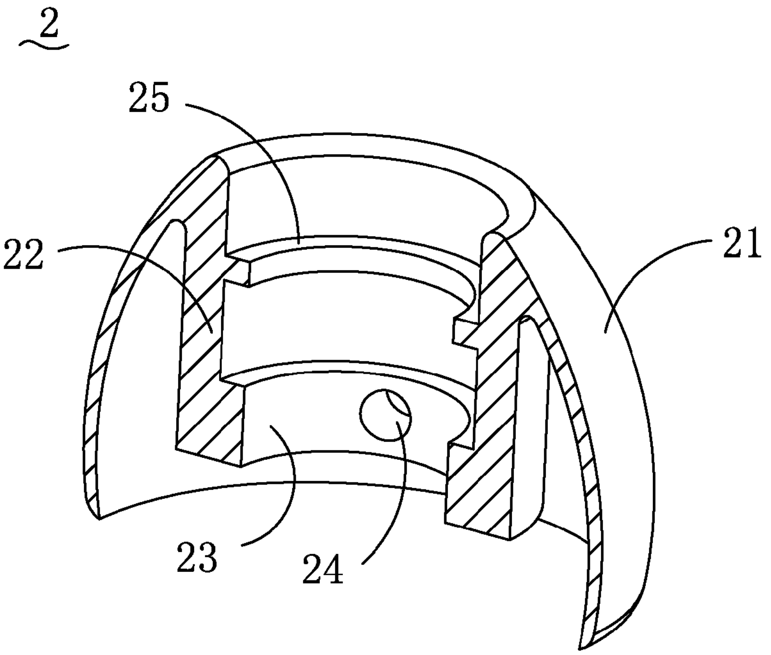
FIG. 3 a partial sectional view of an earphone cap of the earphone of FIG. 1.

Referring to FIGS. 1 and 3, the earphone cap 2 is rotatably mounted on the earphone body 1. The earphone cap 2 includes a main body 21 and a barrel 22, which is located on the inside of the main body 21 and encompasses the sound-guiding pipe 13. The barrel 22 disposes a holding portion 23 protruding on an inner wall thereof and being held into the annular groove 14. The barrel 22 disposes an opening 24 on the holding portion 23. The opening 24 is arranged to be aligned or misaligned with the through hole 15. The barrel 22 forms a recess 25 on one end of the barrel 22. The spacer 3 is placed into the recess 25 to prevent foreign matters from entering into the sound-guiding pipe 13.

In using of the earphone 100 of the present invention, the sound cavity 12 and the sound-guiding pipe 13 are communicated with each other. When needing to adjust the sound effect, the through hole 15 of the earphone shell 11 and the opening 24 of the earphone cap 2 can be aligned or misaligned with each other by rotating the earphone cap 2, so that varying the pressure in the sound cavity 12 to attain the object of adjusting sound effect. Damping objects (not shown in all FIGS), which is made of elastic and compressible material such as sponge, elastic plastic, textile and so on, can be selectable placed into the through hole 15 and the opening 24 for improving the bass effect.

As described above, the earphone 100 of the present invention can make the through hole 15 of the earphone shell 11 be aligned or misaligned with and the opening 24 of the earphone cap 2 by rotating the earphone cap 2, thereby varying the pressure of the sound cavity 12 to attain the object of adjusting sound effect.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. An earphone comprising:

an earphone body, including an earphone shell, which forms a sound cavity in inside thereof and disposes a sound-guiding pipe on one end thereof, wherein the sound-guiding pipe disposes at least one through hole on a sidewall thereof; and an earphone cap, being rotatably mounted on the earphone body and including a main body and a barrel, wherein the barrel is located on the inside of the main body and arranged to encompass the sound-guiding pipe, and the barrel disposes at least one opening, which can be arranged to be aligned or misaligned with the part or whole of the through hole.

2. The earphone as claimed in claim 1, wherein the sound-guiding pipe disposes an annular groove concavely forming on an outer surface thereof, the barrel disposes a holding portion protruding on an inner wall thereof and being held into the annular groove.

3. The earphone as claimed in claim 1, wherein the earphone cap disposes a recess on one end of the barrel, and the earphone further comprises a reticular spacer placed into the recess.

4. The earphone as claimed in claim 1, wherein the through hole and the opening can contain damping objects.

* * * * *